US010551358B2

(12) United States Patent
Meyer et al.

(10) Patent No.: US 10,551,358 B2
(45) Date of Patent: Feb. 4, 2020

(54) SINGLE REACTOR FOR SIMPLIFIED SAMPLE PREPARATION WORKFLOWS

(71) Applicant: Perfinity Biosciences, Inc., West Lafayette, IN (US)

(72) Inventors: Kevin Wayne Meyer, West Lafayette, IN (US); John Patrick O'Grady, West Lafayette, IN (US); Bob Harold Ellis, Half Moon Bay, CA (US); Derrick Nathaniel Poe, West Lafayette, IN (US); Nicholas Brian Herold, West Lafayette, IN (US)

(73) Assignee: Perfinity Bioscices, Inc., West Lafayette, IN (US)

( * ) Notice: Subject to any disclaimer, the term of this patent is extended or adjusted under 35 U.S.C. 154(b) by 271 days.

(21) Appl. No.: 15/101,069

(22) PCT Filed: Dec. 1, 2014

(86) PCT No.: PCT/US2014/067976
§ 371 (c)(1),
(2) Date: Jun. 2, 2016

(87) PCT Pub. No.: WO2015/084748
PCT Pub. Date: Jun. 11, 2015

(65) Prior Publication Data
US 2016/0341704 A1  Nov. 24, 2016

Related U.S. Application Data

(63) Continuation-in-part of application No. PCT/US2014/013782, filed on Jan. 30, 2014.
(Continued)

(51) Int. Cl.
*G01N 30/06* (2006.01)
*G01N 1/40* (2006.01)
(Continued)

(52) U.S. Cl.
CPC ............. *G01N 30/06* (2013.01); *C07K 1/22* (2013.01); *C07K 1/36* (2013.01); *C12M 21/18* (2013.01);
(Continued)

(58) Field of Classification Search
CPC ...... G01N 30/06; G01N 1/405; G01N 1/4044; G01N 1/28; G01N 2030/067; C07K 1/36;
(Continued)

(56) References Cited

U.S. PATENT DOCUMENTS 5,094,819 A    3/1992  Yager et al.
6,432,290 B1 * 8/2002  Harrison ............... B01L 3/5027
                                                        204/451
(Continued)

FOREIGN PATENT DOCUMENTS

WO    WO 2011/112188    9/2011

OTHER PUBLICATIONS

International Search Report and Written Opinion prepared for International Application No. PCT/US14/67976, dated Mar. 5, 2015.
(Continued)

*Primary Examiner* — Michael L Hobbs
(74) *Attorney, Agent, or Firm* — Barnes & Thornburg LLP

(57) ABSTRACT

This disclosure provides a single reactor that accommodates an affinity selector to separate analytes of interest, and an enzyme reactor that digest the analyte to suitable peptides for mass spectrometry. The single reactor formats described herein accommodate workflows wherein separation precedes digestion as well as workflows wherein digestion precedes separation selection.

18 Claims, 5 Drawing Sheets

Specification includes a Sequence Listing.

Flow diagram of affinity selection followed by enzymatic digestion in a single reactor.

Related U.S. Application Data

(60) Provisional application No. 61/911,024, filed on Dec. 3, 2013, provisional application No. 61/954,742, filed on Mar. 18, 2014.

(51) Int. Cl.
    *C12M 1/40*     (2006.01)
    *G01N 1/28*     (2006.01)
    *C12N 15/10*     (2006.01)
    *C07K 1/36*     (2006.01)
    *C07K 1/22*     (2006.01)
    *C12M 1/12*     (2006.01)

(52) U.S. Cl.
    CPC .......... *C12M 23/06* (2013.01); *C12N 15/1003* (2013.01); *G01N 1/28* (2013.01); *G01N 1/405* (2013.01); *G01N 1/4044* (2013.01); *G01N 2030/067* (2013.01)

(58) Field of Classification Search
    CPC .......... C07K 1/22; C12M 23/06; C12M 21/18; C12N 15/1003
    See application file for complete search history.

(56) References Cited

U.S. PATENT DOCUMENTS 6,872,575 B2 * 3/2005 Regnier ............. G01N 33/6803
                                              436/149
2008/0014576 A1 * 1/2008 Jovanovich ......... B01F 11/0071
                                              435/5
2013/0203634 A1 * 8/2013 Jovanovich ....... B01L 3/502738
                                             506/26

OTHER PUBLICATIONS

Supelco Bulletin 910, "Guide to Solid Phase Extraction," published by Sigma Aldrich, 1998, 12 pages.
Tuli, L. et al., "LC-MS Based Detection of Differential Protein Expression," J. Proteomics Bioinform., 2009, 2, 416-438.
International Search Report and Written Opinion prepared for International Application No. PCT/US14/13782, dated Jun. 27, 2014.
Ekstrom, S. et al., "Integrated Microanalytical Technology Enabling Rapid and Automated Protein Identification," Anal. Chem., 2000, 72, 286-293.
Ma, J. et al., "Immobilized enzyme reactors in proteomics," TrAC Trends in Analytical Chemistry, 2011, 30, 691-702.
Sun, L. et al., "High efficiency and quantitatively reproducible protein digestion by trypsin-immobilized magnetic microspheres," J. Chromatography A, 2012, 1220, 68-74.
Pall Corporation, Polypropylene Membranes, 2012, available on the internet: <URL: http://www.pall.com/main/oem-materials-and-devices/printfriendly.page?lid=gri781hg&industry=OEM-materials-and-devices&country=undefined>.

* cited by examiner

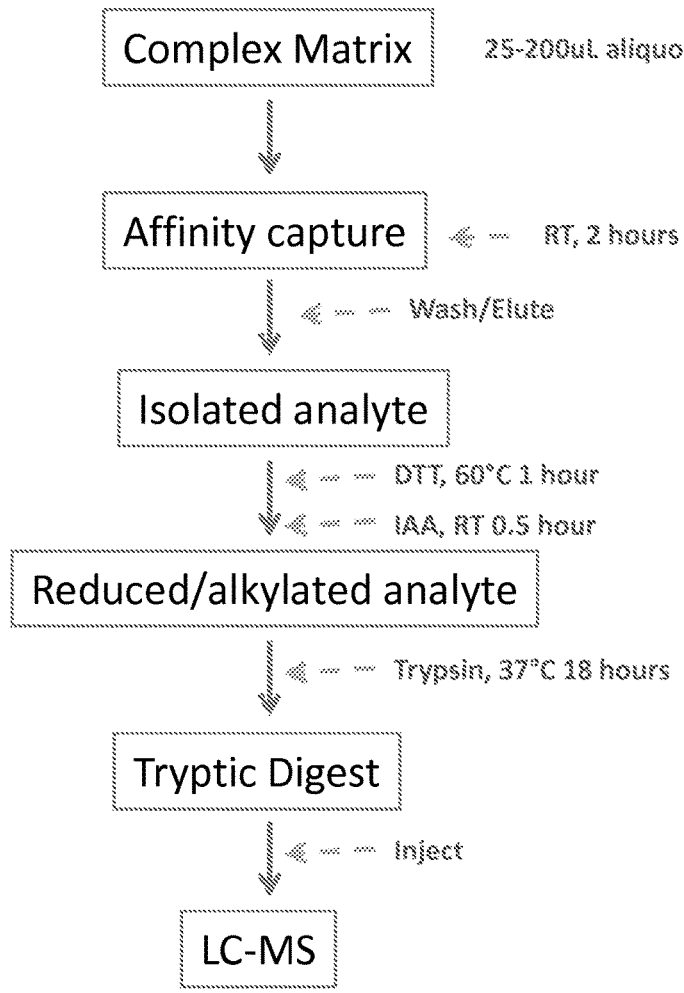
Figure 1: Flow diagram of a common sample preparation workflow used for the purification/enrichment of a protein from a complex mixture followed by enzymatic digestion

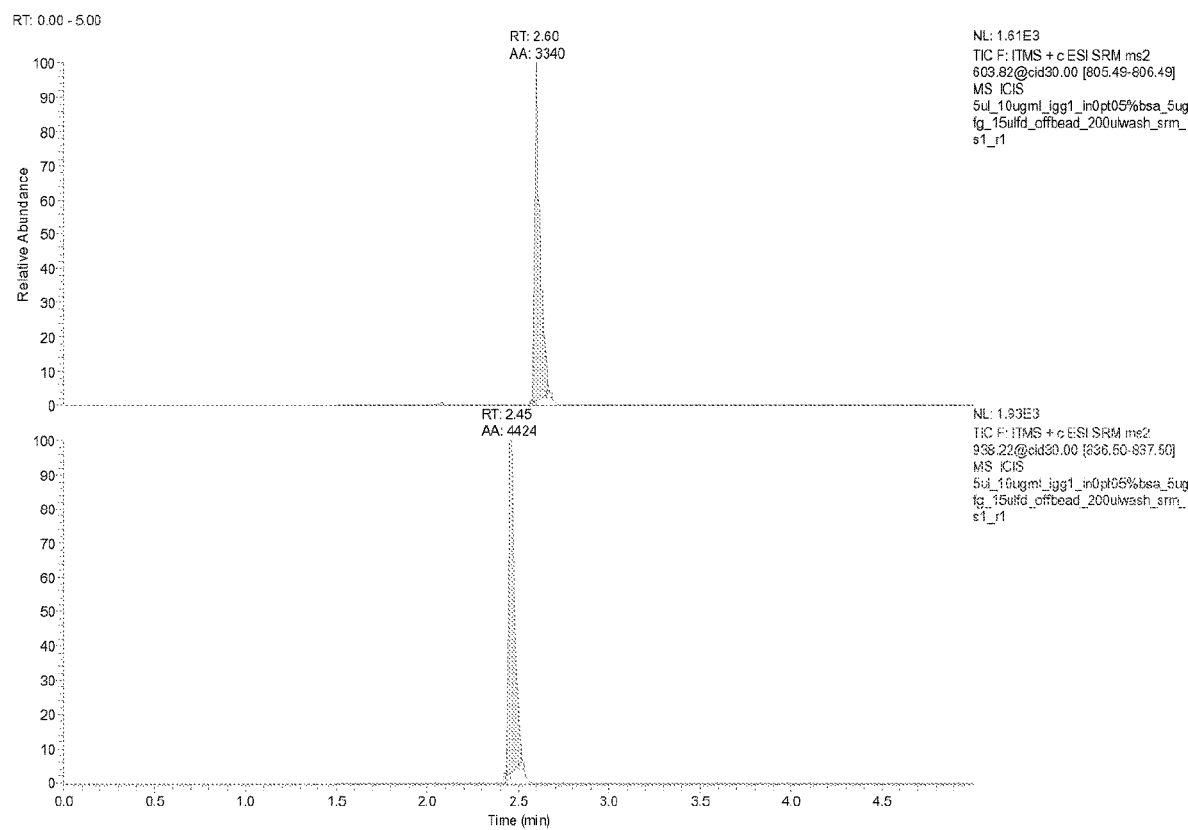
Figure 2: Human IgG1 is affinity purified and digested using a single reaction mixture

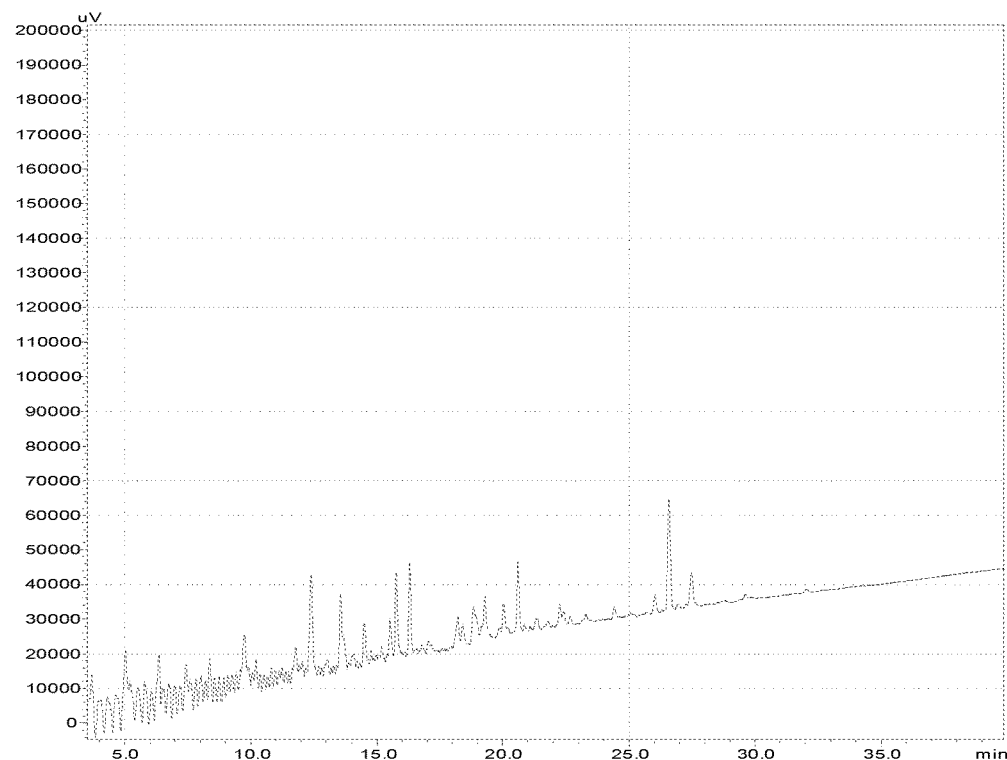
Figure 3: Human IgG1 is affinity purified and digested using a single reaction mixture, no undigested materials are observed.

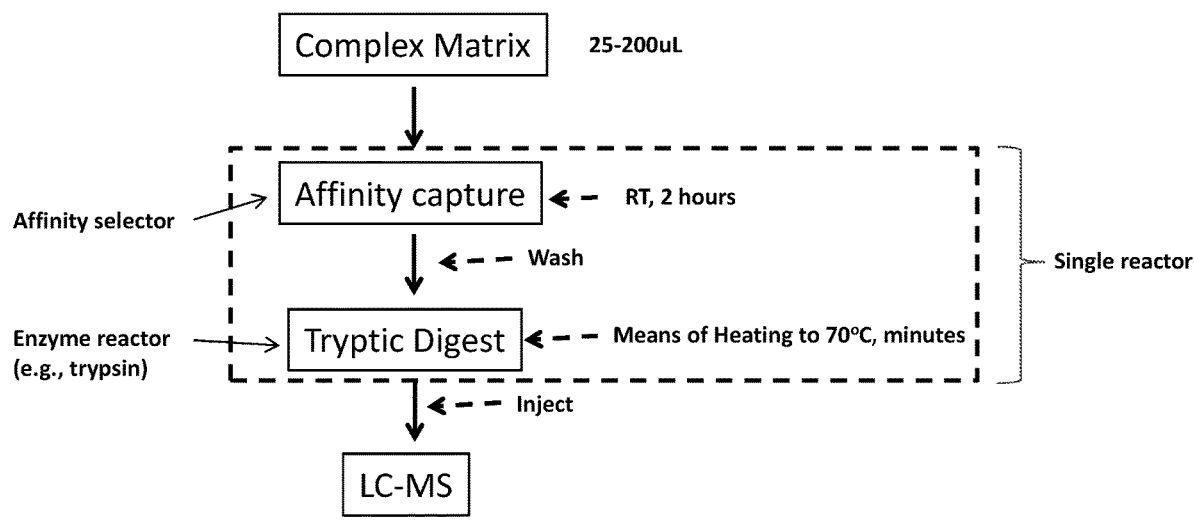
Fig. 4: Flow diagram of affinity selection followed by enzymatic digestion in a single reactor.

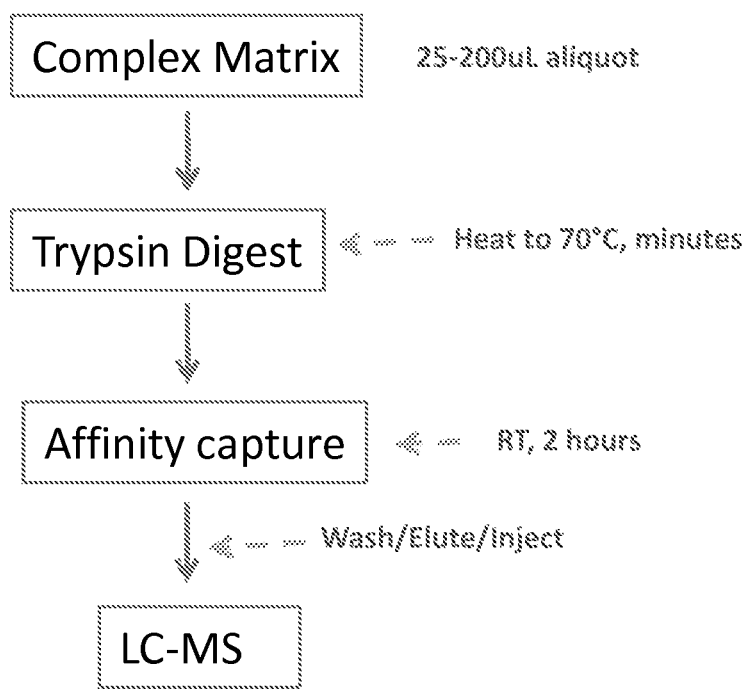
Figure 5: Flow diagram of digestion followed by affinity selection in a single reactor

SINGLE REACTOR FOR SIMPLIFIED SAMPLE PREPARATION WORKFLOWS

CROSS REFERENCE

This application is a national stage entry under 35 U.S.C. § 371(c) of PCT International Application No. PCT/US2014/067976 filed on Dec. 1, 2014, and claims, under 35 U.S.C. § 119(e), the benefit of U.S. provisional application 61/911,024 filed on Dec. 3, 2013, and U.S. provisional application 61/954,742 filed on Mar. 18, 2014, and is a continuation in part of the international application PCT/US14/13782, filed on Jan. 30, 2014. The disclosures therein are incorporated into this application entirely.

FIELD OF INVENTION

This disclosure provides single reactor formats that accommodate both an affinity selector and an enzyme reactor to produce a suitable sample for mass spectrometry analysis. The single reactor formats described herein accommodate workflows wherein separation precedes digestion as well as workflows wherein digestion precedes separation selection.

BACKGROUND

Standard immunoassays have been the dominant method of performing routine serum protein analyses for the last 60 years because they are a conceptually simple method capable of measuring antigens down to the pg/mL level. However, development times for immunoassays are quite long. Furthermore, differences among protein isoforms often occur in small hidden regions of the total structure. Immunological contact areas, epitopes, are also very small, making it difficult to interrogate these variable domains with antibodies. Moreover, antibodies do not clearly discriminate between partial cleavage products, auto-immune complexes, or post-translationally modified proteins. Elucidation of amino acid sequences and identification of post-translational modifications are critical measurements in the determination of protein function and activity. Mass spectrometers are capable of measuring these features, but only when proceeded by robust sample preparation processes.

It is rarely the case that an analyst is presented with a sample in a suitable form for injection into an LC/MS system. Most often the sample must be manipulated in some fashion to concentrate the compound of interest, remove interferences, enzymatically digest the sample to generate surrogate peptides with better mass spectrometric properties and modify the sample matrix/buffering system to achieve compatibility with LC separation and mass spectrometric detection systems (see FIG. 1).

With immunochromatographic analyses, the structural selectivity of antibodies can be used to bind and purify antigens from biological extracts then chromatography used to resolve proteins that differ by only small changes in structure. When combined with mass spectrometry, these methods enable detection of isoform variations and post-translational modifications; identification of these features being key to an understanding of protein function and activity. In a given run, hundreds of peaks can be resolved thus enabling high degrees of multiplexing.

It is frequently the case that affinity selection is performed using antibodies immobilized in a plate, on a surface, on particles or on magnetic beads. In addition, other methods may be used to purify targets with varying degrees of specificity, such as DNA and RNA based affinity systems, peptides, metals, metal oxides, lectins, and lipid binding proteins, as a nonexclusive selection. Furthermore, depending on the resolution of the mass spectrometer it is possible to perform less specific, bulk fractionations based on bulk properties such as size, hydrophilicity, hydrophobicity, charge, diffusion, and ion mobility. The result is that either the desired analytes of interest or undesired impurities in the sample are retained on the stationary phase. (Supelco (1998), *Guide to Solid Phase Extraction*). In a typical workflow, analytes of interest are retained on the stationary phase while the portion that passes through the stationary phase (the flow through) is discarded. In this case, the flow through contains unwanted materials. Once fractionated as such, the analyte of interest is then eluted from the stationary phase. Alternatively, analytes of interest are isolated using a stationary phase with affinity for the unwanted materials in the sample. In this case, the flow through is collected then analyzed.

Concentrating the compound of interest and removing interferences is an integral part of the sample preparation process. However, it is often the case that proteins are reduced to more easily identifiable peptide fragments by cleavage with proteolytic enzymes, the most popular being trypsin (LC-MS Based Detection of Differential Protein Expression, Leepika Tuli and Habtom Ressom J Proteomics Bioinform. 2009 Oct. 2; 2: 416-438). This process is often limited by the inefficiencies of solution digestion. Fundamentally, complete digestion using solution based approached is kinetically unfavorable. The drop in substrate concentration as a digestion nears completion makes it very difficult to obtain complete conversion to product. The process is further complicated by autolysis, a phenomenon that deactivates trypsin and changes its specificity over the course of the reaction.

Typically enzyme produces product at an initial rate that is approximately linear for a short period after the start of the reaction. As the reaction proceeds and substrate is consumed, the rate continuously slows. In order to push reaction kinetics in favor of a complete digestion trypsin can be immobilized onto a solid support. A large category of immobilized enzymes are used in protein chemistry analysis. For example, immobilized trypsin is used in LC/MS routinely to determine protein substrate's constituents. Whether it's a hospital, clinical lab or a biotech firm and whether it is diagnosis, discovery or validation, there are many situations where a quick and accurate contents analysis is beneficial. Traditionally, however, before subjecting the samples to immobilized enzyme reaction, a tedious sample pretreatment process is required. For example, alkylation, reduction or another denaturing maneuver is applied to the samples, often hours or days before analysis can be performed (see FIG. 1). Additionally, separation steps must be followed by an offline addition of reagents. These steps delay time to results while making initial steps in the sample preparation process incompatible with later steps. Ideally, separation and digestion could occur in a single device.

Thus, there is a need to provide a fast, robust and easy to use single reactor that can achieve both the analyte purification and protein digestion at the same reaction vessel. This disclosure provides working examples of such reactor that produces ready to be analyzed peptides in mass spectrometry.

BRIEF DESCRIPTION OF FIGURES

FIG. 1: Flow diagram of a common sample preparation workflow used for the purification/enrichment of a protein from a complex mixture followed by enzymatic digestion.

FIG. 2: Human IgG1 is affinity purified and digested using a single reaction mixture.

FIG. 3: Human IgG1 is affinity purified and digested using a single reaction mixture, no undigested materials are observed.

FIG. 4: Flow diagram of affinity selection followed by enzymatic digestion in a single reactor.

FIG. 5: Flow diagram of digestion followed by affinity selection in a single reactor.

SUMMARY

This disclosure provides a single reactor that performs both affinity purification and enzymatic digestion of protein samples. The single reactor comprised of an affinity selector and an enzyme reactor. The affinity selector retains and purifies at least one analyte of interest through the physical properties of the analyte of interest. The enzyme is kept relatively inactive during the affinity selection.

In some preferred embodiments, the affinity selector and enzyme are co-immobilized in said single reactor.

In some preferred embodiments, the affinity selector and enzyme are partitioned within the single reactor with controlled access to each other.

In the aforementioned single reactor, while the affinity selector is performing, the enzyme is kept relatively inactive during affinity purification steps by means of operation at reduced temperatures, buffer composition, reversible inhibitors, differences in pH, compartmentalization or combinations thereof.

In some embodiments, the aforementioned affinity selector is comprised of protein A, protein G, protein L, antibodies, antibody fragments, biotin, avidin, hydrophobic materials, hydrophilic materials, ionic materials, lectins, metals, metal oxides, lipid binding proteins, chelators, phage display proteins, natural receptors, peptides, synthetic affinity reagents, boronic acid, DNA, RNA, PNA, sugars, or combinations thereof.

In some preferred embodiment, the aforementioned enzyme is selected from the group consisting of enzyme or modified enzyme of: trypsin, chymotrypsin, Lys-C, Glu-C, Arg-C, Asp N, papain, pepsin, elastase, IdeS, pronase and PNGase F or combinations thereof.

In some embodiments, the aforementioned single reactor uses agitation, a pumping system, gravity, osmotic flow, capillary flow, charge, vacuum, positive pressure, centrifugation, or combinations thereof for transferring soluble analytes and working solutions.

In some embodiments, the aforementioned separation or enzyme digestion is further activated or inactivated by means of heat, radiation, sonication (ultrasound), pressure, freeze/thaw, reduction, organic solvent, chaotropic reagents, surfactants, detergents, or any combination thereof.

In some embodiments, the aforementioned affinity selector performs separation either before or after said enzymatic hydrolysis.

In some embodiments, the aforementioned separation or enzyme digestion is aided by using acidic, basic or amphoteric conditions.

In some embodiments, the aforementioned separation or enzymatic digestion is further activated or deactivated by means of changing the temperature.

In some embodiments, the aforementioned single reactor further comprised of a reaction buffer selected from organic solvent, acids, bases, buffers, chaotropic reagents, surfactants, detergents, sugars, sugar alcohols, or combination thereof.

In some embodiments, the aforementioned single reactor is a form of column, membrane, eppendorf tube, pipette tip, multi-well plate, magnetic particle, or combination thereof.

In some embodiments, the aforementioned single reactor comprising supporting material selected from the group consisting of polystyrene, polystyrene/divinylbenzene, silica, controlled porosity glass, dextrans, agarose, acrylates, metals, metal oxides, magnetic support materials, nitrocellulose, or combination thereof.

In some embodiments, a plurality of affinity selectors, enzymes, or combination thereof is used.

In some embodiments, said reactor format is a heater, combination heater/shaker instrument, a heating block on a shaker, shaking in a convection oven, shaking in a water bath, shaking in a microwave oven, shaking in a laser heated reactor or any combination thereof.

In some embodiments, the aforementioned supporting material is in a form of particle, monolithic, membrane, planar or microfluidic channel or magnetic support materials.

In some embodiments, the aforementioned reactor further comprises a liquid permeable barrier and said barrier is sized to enable the passage of said analyte and/or mobile phases while precluding the passage of stationary phases.

In some embodiments, the aforementioned purified analyte of interest is treated by reductive alkylation either before or after digestion.

In some embodiments, the aforementioned reactor is operated under dynamic or static heating/shaking conditions.

These and other features, aspects and advantages of the present invention will become better understood with reference to the following figures, associated descriptions and claims.

DETAILED DESCRIPTION AND PREFERRED EMBODIMENTS

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

Unless defined otherwise, the scientific and technology nomenclatures have the same meaning as commonly understood by a person in the ordinary skill in the art pertaining to this disclosure.

Various Reactor Formats

Tube Format

In one format, a single reaction vessel containing both a separation device and an immobilized enzyme is used. The separation occurs under conditions at which the immobilized enzyme reactor is relatively inactive, but once activated, the immobilized enzyme is capable of performing digestion without pretreatment.

Co-Immobilization

In one format, a single reaction vessel is used where the separation materials and the immobilized enzyme share a single surface. Again, the separation can occur where the immobilized enzyme reactor is relatively inactive, but once activated is capable of performing digestion without pretreatment.

Partitioned Immobilization

In one format, a single reaction vessel is used where both the separation materials and the immobilized enzyme are on two separate supporting materials with restricted access to each other. The separation can occur where the immobilized enzyme reactor is relatively inactive but once activated capable of performing digestion without pretreatment. Alternatively, the digestion can occur under harsh conditions. Such harsh conditions do not affect the protected separation materials that enable the separation of peptides following digestion.

Separation Capture in the Presence of an Inhibitor

In one format, a single reaction vessel contains both a separation device and an immobilized enzyme. The separation occurs in the presence of a reversible inhibitor such that during separation the immobilized enzyme reactor is relatively inactive. Following the separation, a wash step would remove the reversible inhibitor, enabling digestion to proceed.

Separation and Digestion Under Varying pH Conditions

In one format, a single reaction vessel contains both a separation device and an immobilized enzyme. The separation occurs at a certain pH condition such that during separation the immobilized enzyme reactor is relatively inactive at the specific pH. Following separation, a wash step changes the pH to a level enabling the enzyme digestion to proceed.

Digestion That Precedes Separation

In one format, a single reaction vessel contains both a separation device and an immobilized enzyme. The digestion occurs first, followed by separation of the peptide products based on differences in affinity for the separation devices. In such cases it is important that the affinity selection device be unaffected by digestion. An example would be protein digestion followed by ion exchange separation, immobilized metal affinity chromatography (IMAC) or SOLID PHASE EXTRACTION (SPE).

Compartmentalized Separation and Digestion

In one format, a single reaction vessel contains both a separation device and an immobilized enzyme, with the two being separated by a removable barrier (e.g. a wax). While the separation occurs the immobilized enzyme is separated from the materials to be separated. Once separation has been completed, the barrier is removed (e.g. melted in the case of wax). The separated materials and the immobilized enzyme materials are free to interact and digestion able to proceed.

Separation and Digestion in a Single Reactor With Flow

In one format, a single reaction vessel contains both a separation device and an immobilized enzyme with flow passing over both the separation and immobilized materials.

The mobile phase contains either a reversible inhibitor of the enzyme or alternatively be kept at a low temperature so as to minimize enzyme activity. Once separation has occurred, the reversible inhibitor is removed and/or the temperature is elevated so as to initiate digestion.

Described below is the development of an immobilized enzyme reactor that is inactive at low temperatures but once heated capable of performing digestion without pretreatment. This reactor is also combined with, in this example, affinity separation. As such, a single reactor is used for a purification process at typical low temperature conditions, followed by an activation of digestion.

Example 1: Synthesis of Aldehyde Starting Materials

In 50 mL reaction vessel were added 1.334 mL epibromohydrin, 0.666 mL glycidol, 15 mL dichloromethane and 50 uL boron trifluoride etherate. This reaction was allowed to incubate at room temperature for 24 hrs. After 24 hours the solvent was removed en vacuo. To this same reaction vessel 10 mL $dH_2O$, 7 mL polyethylene glycol, 30 mL IPA and 3 g PS-DVB were added. This flask was gently agitated for 14 hours. The resulting coated particles were filtered and collected in a clean round bottom flask. 10 mL 2 M KOH was added and the mixture gently agitated for 2 hours. After 2 hours 2 g sorbitol was added and the mixture gently agitated at room temperature for 12 hours. After 12 hours this mixture was filtered, washed with water and transferred to a clean round bottom flask. 100 mg sodium periodate was added to these materials and the resulting mixture incubated for 1 hour at room temperature. After 1 hour these materials were washed with 20 mL 50 mM sodium carbonate, filtered collected into a large eppendorf.

Example 2: Synthesis of Co-Immobilized Affinity Selector (Avidin) and Temperature Stable Enzyme Reactor Add the following to a 50 mL eppendorf, 0.1 g aldehyde resin, 7.5 mg porcine trypsin solution (200 uL, 37.5 mg/mL in carbonate buffer, 10 mg/mL benzamidine), 5 mg avidin (500 uL, 10 mg/mL in carbonate buffer) 0.48 mL $Na_2SO_4$ solution (137.5 mg/mL in carbonate buffer), 54 uL $NaBH_3CN$ solution (20 mg/mL in carbonate buffer), 0.82 mL 0.1 M carbonate buffer. Shake end over end and incubate at room temperature on orbital shaker for 2 hrs. Add 166.8 uL AANHS solution (40 mg/mL in DMSO), shake end over end and incubate at room temperature on orbital shaker for 1 hrs. Centrifuge resin (2500 RPM for 1 minute) & decant 1.4 mL, add 3 mL TBS. Centrifuge resin (2500 RPM for 1 minute) & decant 2.4 mL, add 2.4 mL TBS. To eppendorf containing resin in TBS, added 54 uL (20 mg/mL) $NaBH_3CN$ solution. Allow this solution to react for 2 hours RT on orbital shaker. Centrifuge resin (2500 RPM for 1 minute) & decant 2.4 mL, add 2.4 mL TBS with 0.02% azide. Centrifuge resin (2500 RPM for 1 minute) & decant 2.4 mL, add 0.90 mL TBS with 0.02% azide.

To make the single reactor with co-immobilized enzyme/affinity selector, 30 uL of co-immobilized affinity selector/enzyme prepared as described above was slurry packed into each well of a strip of 8 PCR tube. Without wishing to be limited to theory, the immobilized enzyme is largely inert at low temperatures. As such affinity selection can be performed prior to enzymatic digestion of the selected materials (e.g. analyte). Following affinity selection, enzymatic digestion of the selected materials can be performed by simply activating the digestion by means of heating the reactor.

Example 3: Synthesis of Co-Immobilized Affinity Selector (Protein G) and Temperature Stable Enzyme Reactor Add the following to a 50 mL eppendorf, 0.1 g aldehyde resin, 7.5 mg porcine trypsin solution (200 uL, 37.5 mg/mL in carbonate buffer, 10 mg/mL benzamidine), 5 mg Protein G (1.25 mL, 4 mg/mL in PBS) 0.48 mL $Na_2SO_4$ solution (137.5 mg/mL in carbonate buffer), 54 uL $NaBH_3CN$ solution (20 mg/mL in carbonate buffer), 0.07 mL 0.1 M carbonate buffer. Shake end over end and incubate at room temperature on orbital shaker for 2 hrs. Add 166.8 uL AANHS solution (40 mg/mL in DMSO), shake end over end and incubate at room temperature on orbital shaker for 1 hrs. Centrifuge resin (2500 RPM for 1 minute) & decant 1.4 mL, add 3 mL TBS. Centrifuge resin (2500 RPM for 1 minute) & decant 2.4 mL, add 2.4 mL TBS. To eppendorf containing resin in TBS, added 54 uL (20 mg/mL) $NaBH_3CN$ solution. Allow this solution to react for 2 hours RT on orbital shaker. Centrifuge resin (2500 RPM for 1 minute) & decant 2.4 mL, add 2.4 mL TBS with 0.02% azide. Centrifuge resin (2500 RPM for 1 minute) & decant 2.4 mL, add 0.90 mL TBS with 0.02% azide.

To make the single reactor with co-immobilized enzyme/affinity selector, 30 uL of co-immobilized affinity selector/enzyme prepared as described above was slurry packed into each well of a strip of 8 PCR tube. Without wishing to be limited to theory, the immobilized enzyme is largely inert at low temperatures. As such affinity selection can be performed prior to enzymatic digestion of the selected materials (e.g. analyte). Following affinity selection, enzymatic digestion of the selected materials can be performed by simply activating the digestion by means of heating the reactor.

Example 4: Synthesis of Temperature Stable Enzyme IMER

Add the following to a 50 mL eppendorf, 0.5 g aldehyde resin, 100 mg porcine trypsin, 2 mL of 20 mg/mL benzamidine solution, 2.4 mL (142 mg/mL) $Na_2SO_4$ solution, 270 uL (20 mg/mL) $NaBH_3CN$ solution, 5.6 mL 0.1 M carbonate buffer. Shake end over end and incubate at room temp. on orbital shaker for 4 hrs. Add 667 uL (40 mg/mL) AANHS solution, shake end over end and incubate at room temp. on orbital shaker for 1 hrs. Centrifuge resin (2500 RPM for 1 minute) & decant 7 mL, add 15 mL TBS. Centrifuge resin (2500 RPM for 1 minute) & decant 12 mL, add 12 mL TBS. To eppendorf containing resin in TBS, added 270 uL (20 mg/mL) $NaBH_3CN$ solution. Allow this solution to react for 2 hours RT on orbital shaker. Centrifuge resin (2500 RPM for 1 minute) & decant 12 mL, add 12 mL TBS with 0.02% azide. Centrifuge resin (2500 RPM for 1 minute) & decant 12 mL, add 4.5 mL TBS with 0.02% azide.

Example 5: Synthesis of Affinity Selector

To a 15 mL Eppendorf tube add 25 mg protein G, 0.125 g aldehyde resin, 0.6 mL $Na_2SO_4$ (137.5 mg/mL in PBS), 70 uL $NaBH_3CN$ solution (20 mg/mL in PBS), 0.9 mL 0.1 M PBS and incubate end over end at room temp for 18 hours. Centrifuge resin (2500 RPM for 1 minute) & decant 1.75 mL, add 3.75 mL TBS, Centrifuge resin (2500 RPM for 1 minute) & decant 3 mL, add 3 mL TBS. Add 70 uL $NaBH_3CN$ solution (20 mg/mL in PBS) and incubate end over end at room temp for 2 hours. Centrifuge resin (2500 RPM for 1 minute) & decant 3 mL, add 1.125 mLTBS. Centrifuge resin (2500 RPM for 1 minute) & decant 5 mL, add 5 mL TBS. Centrifuge resin (2500 RPM for 1 minute) & decant 4 mL. Make 1 mL aliquots, centrifuge then decant 750 uL buffer and leave as a slurry.

Example 6: Making a Partitioned Affinity Selector (Protein G) and Temperature Stable Enzyme To a 15 mL Eppendorf tube add 0.05 g aldehyde resin 10 mg avidin, 0.24 mL $Na_2SO_4$ (137.5 mg/mL in carbonate buffer pH 8), 27 uL $NaBH_3CN$ solution (20 mg/mL in carbonate buffer), 0.560 mL carbonate buffer and incubate end over end at room temp for 5 hours. Centrifuge resin (2500 RPM for 1 minute) & decant 0.7 mL, add 1.5 mL TBS. Centrifuge resin (2500 RPM for 1 minute) & decant 1.2 mL, add 1.2 mL TBS. Add 27 uL $NaBH_3CN$ solution (20 mg/mL in TBS) and incubate end over end at room temp for 2 hours. Centrifuge resin (2500 RPM for 1 minute) & decant 1.2 mL, add 1.2 mL TBS. Centrifuge resin (2500 RPM for 1 minute) & decant 1.2 mL, add 0.45 mL TBS.

Add the following to a 50 mL eppendorf, 0.05 g aldehyde resin, 7.5 mg porcine trypsin solution (200 uL, 37.5 mg/mL in carbonate buffer, 20 mg/mL benzamidine), 0.24 mL (142 mg/mL) $Na_2SO_4$ solution (142 mg/mL in carbonate buffer, 27 uL $NaBH_3CN$ solution (20 mg/mL in carbonate buffer), 0.560 mL 0.1 M carbonate buffer. Shake end over end and incubate at room temperature on orbital shaker for 4 hrs. Add 66.5 uL AANHS solution (40 mg/mL in DMSO), shake end over end and incubate at room temperature on orbital shaker for 1 hrs. Centrifuge resin (2500 RPM for 1 minute) & decant 0.7 mL, add 1.5 mL TBS. Centrifuge resin (2500 RPM for 1 minute) & decant 1.2 mL, add 1.2 mL TBS. To eppendorf containing resin in TBS, added 27 uL (20 mg/mL) $NaBH_3CN$ solution. Allow this solution to react for 2 hours RT on orbital shaker. Centrifuge resin (2500 RPM for 1 minute) & decant 1.2 mL, add 1.2 mL TBS with 0.02% azide. Centrifuge resin (2500 RPM for 1 minute) & decant 1.2 mL, add 0.45 mL TBS with 0.02% azide.

To make the single reactor with partitioned enzyme/affinity selector, 15 uL of immobilized avidin prepared as described above and 15 uL of immobilized trypsin prepared as described above was slurry packed into each well of a strip of 8 PCR tube. Without wishing to be limited to theory, the majority of the surface area of these materials is thought to reside with the pores of the respective materials. As such, only a small portion of the immobilized affinity selector is exposed to the immobilized enzyme. Concomitantly, only a small portion of the immobilized enzyme is exposed to the immobilized affinity selector.

Example 7: Use of Decreased Temperature to Keep Enzyme Relatively Inactive

In this example, a combined single reactor with both affinity selection means and a heat activated enzyme digestion reactor is provided for producing desirable peptides to be analyzed in mass spectrometry. The use of decreased temperature (e.g. operation at 20° C.) is shown to keep the temperature stable enzyme reactor enzyme relatively inactive.

Briefly, the reactors were prepared by adding 30 uL of co-immobilized affinity selector (avidin) and temperature stable enzyme reactor materials prepared according to Example 2 to each of 2 1.5 mL Eppendorf tubes. 400 uL of a 1 ug/mL sample of IgG1 in an optimized digestion buffer (50 mM Tris, 500 mM $CaCl_2$, 10% glycerol) were added to each tube. The samples were incubated with shaking for 2 hour at room temperature (20° C.) or 70° C. The samples were then centrifuged and decanted. The supernatants were then analyzed by LCMS using the parameters detailed in Table 1. The results, showing the inactivity of the room temperature reactor, are given in Table 2.

TABLE 1

LC/MS parameters for analysis of temperature differentiated digested IgG₁ Sample

| | |
|---|---|
| Injection Volume | 5 uL |
| Reversed Phase A | 2% ACN (aq) 0.1% Formic Acid |
| Reversed Phase B | 90% ACN (aq) 0.1% Formic Acid |
| Reversed Phase Gradient | 2-70%B in 5 minutes |
| MS1/MS2 | SEQ ID NO: 2 TTPPVLDSDGSFFLYSK-938/837 |

TABLE 2

The impact of temperature on immobilized enzyme reactor enzyme activity

| Analyte incubation temperature | m/z = 938 Peak Area |
|---|---|
| 70° C. | 22862 |
| Room Temperature (20° C.) | 3144 |

Example 8: Use of Buffer to Keep Enzyme Inactive During Affinity Selection

In this example, a combined single reactor with both affinity selection means and a heat activated enzyme digestion reactor is provided for producing desirable peptides to be analyzed in mass spectrometry. The use of buffer selection is shown to keep the temperature stable enzyme reactor enzyme relatively inactive.

Briefly, the reactors were prepared by adding 30 uL of co-immobilized affinity selector (avidin) and temperature stable enzyme reactor materials prepared according to Example 2 to each of 2 1.5 mL Eppendorf tubes. 400 uL of a 1 ug/mL sample of IgG1 in an optimized digestion buffer or 50 mM Tris were added to each tube. The samples were incubated with shaking for 2 hour at 70° C. The samples were then centrifuged and decanted. The supernatants were then analyzed by LCMS using the parameters detailed in Table 3. The results, showing the inactivity of the 50 mM Tris reactor, are given in Table 4.

TABLE 3

LC/MS parameters for analysis of buffer differentiated digested IgG₁ Sample

| | |
|---|---|
| Injection Volume | 5 uL |
| Reversed Phase A | 2% ACN (aq) 0.1% Formic Acid |
| Reversed Phase B | 90% ACN (aq) 0.1% Formic Acid |
| Reversed Phase Gradient | 2-70%B in 5 minutes |
| MS1/MS2 | SEQ ID NO: 2 TTPPVLDSDGSFFLYSK-938/837 |

TABLE 4

| | | |
|---|---|---|
| The impact of buffer selection on immobilized enzyme reactor enzyme activity | | |
| Analyte incubation temperature | | m/z = 938 Peak Area |
| Optimized Digestion buffer | | 22862 |
| Tris (50 mM) | | 0 |

Example 9: A Combined Affinity Selector/Enzyme Reactor

In this example, a combined single reactor with both affinity selection means and a heat activated enzyme digestion reactor is provided for producing desirable peptides to be analyzed in mass spectrometry. See FIG. 2: Human IgG1 is affinity purified and digested using a single reaction mixture and FIG. 3: Human IgG1 is affinity purified and digested using a single reaction mixture, no undigested materials are observed.

Briefly, the reactor was prepared by adding 5 uL of Protein G materials and 15 uL of immobilized enzyme materials prepared as described above to each well of a 2 mL polypropylene microtiter plate. 200 uL of a 100 ug/mL sample of IgG1 was added to the microtiter plate. The sample was incubated with shaking for 1 hour at room temperature. The entire sample was filtered through a filter plate. 200 uL of digest buffer was added to the filter plate, mixed via repeat pipetting, and then transferred to a PCR tube. This PCR tube was incubated at 1400 RPM for 60 minutes at 70° C. The PCR tube was removed the sample filtered and the filtrate analyzed by LCMS.

TABLE 5

| LC/MS parameters for analysis of affinity selected then digested IgG$_1$ Sample | |
|---|---|
| | Affinity selected, then digested IgG$_1$ |
| Injection Volume | 10 uL |
| Reversed Phase A | 2% ACN (aq) 0.1% Formic Acid |
| Reversed Phase B | 90% ACN (aq) 0.1% Formic Acid |
| Reversed Phase Gradient | 2-70%B in 5 minutes |
| MS1/MS2 | SEQ ID NO: 1 TTPPVLDSDGSFFLYSK-938/837 |
| MS1/MS2 | SEQ ID NO: 2 VVSVLTVLHQDWLNGK-603.67/805.62 |

TABLE 6

| LC/UV/VIS parameters for analysis of affinity selected then digested IgG$_1$ | |
|---|---|
| Sample | Affinity selected, then digested IgG$_1$ |
| Injection Volume | 50 uL |
| Reversed Phase A | 2% ACN (aq) 0.1% TFA |
| Reversed Phase B | 90% ACN (aq) 0.1% TFA |
| Reversed Phase Gradient | 2-70% B in 40 minutes |
| UV/VIS | 214 nm |

Example 10: Use of a Single Reactor Containing Co-Immobilized Affinity Selector/Enzyme for Purification of IgG From a Bovine Serum Albumin Solution Followed by Digestion In this example, a combined single reactor with both affinity selection means and a heat activated enzyme digestion reactor is provided for producing desirable peptides to be analyzed in mass spectrometry.

Briefly, the reactor was prepared by adding 30 uL of co-immobilized affinity selector/enzyme prepared as described above into each well of a strip of 8 PCR tube. 200 uL of a biotinylated IgG1 at concentrations ranging from in 0.5% BSA was added to the tubes. The reactor was incubated with shaking for 1 hour at room temperature. Following incubation, the reactor was centrifuged, 150 uL of solution decanted from each well and 150 uL of TBS buffer added to each well. The reactor was centrifuged again. Following centrifugation, 150 uL of solution decanted from each well and 150 uL of TBS buffer added to each well and the reactor transferred to a ThermoMixer C equipped with a PCR block. The strip of 8 was then incubated at 70° C. and shaken at 1400 revolutions per minute for 45 minutes. Following this incubation the reaction vessel was centrifuged, 150 uL of the digested materials transferred to a polypropylene plate, diluted with an additional 150 uL TBS buffer and then analyzed by LCMS.

Example 11: Use of a Single Reactor Containing Co-Immobilized Affinity Selector/Enzyme for Purification of IgG From Plasma Followed by Digestion In this example, a combined single reactor with both affinity selection means and a heat activated enzyme digestion reactor is provided for producing desirable peptides to be analyzed in mass spectrometry.

Briefly, the reactor was prepared by adding 30 uL of co-immobilized affinity selector/enzyme prepared as described above into 1.5 mL eppendorf tubes. 400 uL of human IgG1 at concentrations ranging from 5 ng/mL to 5000 ng/mL in murine plasma was added to the tubes. 8 uL of 0.5 mg/mL biotinylated anti-human IgG antibodies were also added to the tubes. The reactor was incubated with shaking for 2 hours at room temperature. Following incubation, the reactor was centrifuged, 150 uL of solution decanted from each well and 350 uL of TBS buffer added to each well. The reactor was centrifuged again. Following centrifugation, 350 uL of solution decanted from each well and 350 uL of TBS buffer added to each well. This was repeated 3 more times. Following the 5' centrifugation 350 uL of solution was decanted from each well, 150 uL of optimized digestion buffer was added and the reactors were

TABLE 7

LC/MS parameters for analysis of affinity selection followed by digestion of IgG$_1$ using co-immobilized affinity selector/enzyme

| | |
|---|---|
| Injection Volume | 10 uL |
| Reversed Phase A | 2% ACN (aq) 0.1% Formic Acid |
| Reversed Phase B | 90% ACN (aq) 0.1% Formic Acid |
| Reversed Phase Gradient | 2-70%B in 5 minutes |
| MS1/MS2 | SEQ ID NO: 1 TTPPVLDSDGSFFLYSK-938/837 |
| MS1/MS2 | SEQ ID NO: 2 VVSVLTVLHQDWLNGK-603.67/805.62 |

TABLE 8

Results from the LC/MS analysis of affinity selection followed by digestion of IgG$_1$ using co-immobilized affinity selector/enzyme

| Analyte | m/z = 938 | | | | | | |
|---|---|---|---|---|---|---|---|
| Peptide Concentration | 10 | 32 | 100 | 320 | 1000 | 3200 | 10000 |
| Units | (ng/mL) | (ng/mL) | (ng/mL) | (ng/mL) | (ng/mL) | (ng/mL) | (ng/mL) |
| Peak Area | 1297 | 1486 | 2472 | 8004 | 23862 | 80081 | 272054 |
| Analyte | m/z = 603 | | | | | | |
| Peptide Concentration | 10 | 32 | 100 | 320 | 1000 | 3200 | 10000 |
| Units | (ng/mL) | (ng/mL) | (ng/mL) | (ng/mL) | (ng/mL) | (ng/mL) | (ng/mL) |
| Peak Area | 137 | 262 | 897 | 3297 | 12077 | 38083 | 130229 |

These results further suggest the immobilized enzyme is largely inert at low temperatures. As such affinity selection can be performed prior to enzymatic digestion of the selected materials (e.g. analyte). Following affinity selection, enzymatic digestion of the selected materials can be performed by simply by activating the digestion by means of heating the reactor.

transferred to a ThermoMixer C equipped with a 1.5 mL block. They were then incubated at 70° C. and shaken at 1400 revolutions per minute for 1 hour. Following this incubation the reaction vessel was centrifuged, 175 uL of the digested materials transferred to a polypropylene plate and then analyzed by LCMS. FIG. 4 is a schematic of this workflow.

TABLE 9

LC/MS parameters for analysis of IgG purified from plasma then digestion using a single reactor containing co-immobilized affinity selector and enzyme

| | |
|---|---|
| Injection Volume | 25 uL |
| Reversed Phase A | 2% ACN (aq) 0.1% Formic Acid |
| Reversed Phase B | 90% ACN (aq) 0.1% Formic Acid |
| Reversed Phase Gradient | 2-70%B in 5 minutes |
| MS1/MS2 | SEQ ID NO: 1 TTPPVLDSDGSFFLYSK-938/837 |
| MS1/MS2 | SEQ ID NO: 2 VVSVLTVLHQDWLNGK-603.67/805.62 |

TABLE 10

Results from the analysis of IgG purified from plasma then digested using a single reactor containing co-immobilized affinity selector and enzyme

| Analyte | m/z = 938 | | | | | | |
|---|---|---|---|---|---|---|---|
| Peptide Concentration | 5 | 15.8 | 50 | 158 | 500 | 1580 | 5000 |
| Units | (ng/mL) | (ng/mL) | (ng/mL) | (ng/mL) | (ng/mL) | (ng/mL) | (ng/mL) |
| Peak Area | 1728 | 7934 | 20376 | 62773 | 186918 | 548938 | 1187476 |
| Analyte | m/z = 603 | | | | | | |
| Peptide Concentration | 5 | 15.8 | 50 | 158 | 500 | 1580 | 5000 |
| Units | (ng/mL) | (ng/mL) | (ng/mL) | (ng/mL) | (ng/mL) | (ng/mL) | (ng/mL) |
| Peak Area | 3655 | 10095 | 29321 | 89187 | 252593 | 656136 | 1532738 |

Example 12: A Comparison of the Use of Co-Immobilized Affinity Selector/Enzyme and Partitioned Affinity Selector/Enzyme In this example, a combined single reactor with both affinity selection means and a heat activated enzyme digestion reactor is provided for producing desirable peptides to be analyzed in mass spectrometry.

Briefly, the co-immobilized reactor was prepared by adding 30 uL of co-immobilized affinity selector/enzyme prepared as described above into each well of a strip of 8 PCR tube. The partitioned reactor was prepared by adding 15 uL of immobilized affinity selector and 15 uL immobilized enzyme prepared as described above into each well of a strip of 8 PCR tube.

200 uL of a 10 ug/mL biotinylated IgG1 was added to 2 wells of each of the reactors. Each reactor was incubated with shaking for 1 hour at room temperature. Following incubation, the reactors were centrifuged, 150 uL of solution decanted from each well and 150 uL of TBS buffer added to each well. The reactors were centrifuged again. Following centrifugation, 150 uL of solution decanted from each well and 150 uL of TBS buffer added to each well and the reactors transferred to a ThermoMixer C equipped with a PCR block. The reactors were then incubated at 70° C. and shaken at 1400 revolutions per minute for 45 minutes. Following this incubation the reaction vessel was centrifuged, 150 uL of the digested materials decanted from each well and transferred to a polypropylene plate, diluted with an additional 150 uL TBS buffer and then analyzed by LCMS.

TABLE 11

LC/MS parameters for the comparative analysis of samples prepared by means of co-immobilized affinity selector/enzyme and partitioned affinity selector/enzyme

| | |
|---|---|
| Injection Volume | 10 uL |
| Reversed Phase A | 2% ACN (aq) 0.1% Formic Acid |
| Reversed Phase B | 90% ACN (aq) 0.1% Formic Acid |
| Reversed Phase Gradient | 2-70%B in 5 minutes |
| MS1/MS2 | SEQ ID NO: 1 TTPPVLDSDGSFFLYSK-938/837 |
| MS1/MS2 | SEQ ID NO: 2 VVSVLTVLHQDWLNGK-603.67/805.62 |

TABLE 12

Results from the comparative analysis of samples prepared by means of co-immobilized affinity selector/enzyme and partitioned affinity selector/enzyme

| Analyte | m/z = 938 Peak Area | m/z = 603 Peak Area |
|---|---|---|
| Co-immobilized Affinity Selector/Enzyme | 1072859 | 378210 |
| Partitioned Affinity Selector/Enzyme | 131673 | 15752 |

These results suggest that only a small portion of the immobilized affinity selector is exposed to the immobilized enzyme and only a small portion of the immobilized enzyme is exposed to the immobilized affinity selector. This functionality is important in cases where affinity selection is performed following digestion (FIG. 11). In these cases the affinity selector can be added to the reaction, protected by means of partitioning during the reaction, then able to proceed uninhibited as peptide analytes of interest are generated during the digestion process. Alternatively, the use of a robust, extremely stable, easily modified affinity support such as avidin would also enable the addition of biotinylated antibodies following digestion. This would be especially useful in situations where the antibody used for peptide capture might be denatured by means of the heat used during digestion.

These results also show the dramatic increase in interaction and solubilization effect achieved by means of bringing the immobilized enzyme in close proximity to the analyte target of interest. This solubilizing effect may be beneficial in a number of applications where the proteins of interest are difficult to solubilize; for example, if they have been dried down or precipitated out. In these cases, bringing the difficult to solubilize materials in close contact with the enzyme and then converting the proteins into more soluble peptides can be used as a strategy for solubilization.

It should be understood that the foregoing relates to exemplary embodiments of the disclosure and that modifications may be made without departing from the spirit and scope of the invention as set forth in the following claims.

The invention claimed is:

1. A single reactor wherein said single reactor performs affinity purification, separation, and enzymatic digestion of protein samples, comprising:
   an affinity selector and an enzyme reactor that are co-immobilized on a supporting material within a single reaction vessel,
   wherein the affinity selector retains and purifies at least one analyte of interest through physical properties of the analyte of interest; and
   wherein the enzyme reactor comprises an enzyme of interest that is kept relatively inactive during affinity selection that is selected from the group consisting of trypsin, chymotrypsin, Lys-C, Gluc-C, Arg-C, Asp N, papin, pepsin, elastase, IdeS, pronase, PNGase F, modified trypsin, modified chymotrypsin, modified lys-C, modified Gluc-C, modified Arg-C, modified Asp N, modified papain, modified pepsin, modified elastase, modified IdeS, modified pronase, modified PNGase F, and combinations thereof, and
   wherein the single reactor further comprises a means of heating said enzyme of interest selected from the group consisting of a heater, a combination heater/shaker instrument, a heating block on a shaker, a convection oven, a water bath, a microwave oven, a laser heated reactor or any combination thereof to produce an activated enzyme.

2. The single reactor according claim 1, wherein the enzyme of interest is kept relatively inactive during affinity purification steps by means of operation at reduce temperatures, buffer composition reversible inhibitors, differences in pH, compartmentalization or combinations thereof.

3. The single reactor according to a claim 1, wherein the affinity selector is comprised of protein A, protein G, protein L, antibodies, antibody fragments, biotin, avidin, hydrophobic materials, hydrophilic materials, ionic materials, lectins, metals, metal oxides, lipid binding proteins, chelators, phage display proteins, natural receptors, peptides, synthetic affinity reagents, boronic acid, DNA, RNA, PNA, sugars or combinations thereof.

4. The single reactor according to claim 1, wherein the single reactor uses agitation, a pumping system, gravity, osmotic flow, capillary flow, charge, vacuum, positive pressure, centrifugation, or combinations thereof for transferring soluble enzymes and working solutions.

5. The single reactor according to claim 1, wherein the heat further comprises radiation, sonication and pressure or any combination thereof.

6. The single reactor according to claim 1, wherein the affinity selector performs separation either before or after said enzymatic hydrolysis.

7. The single reactor according to claim 1, wherein said separation or enzyme digestion is aided by using acidic, basic or amphoteric conditions.

8. The single reactor according to claim 1, wherein the enzyme of interest is inactivated by freeze/thaw, reduction of temperature, organic solvent, chaotropic reagents, surfactants, and detergents or any combination thereof.

9. The single reactor according to claim 1, further comprising a reaction buffer selected from organic solvent, acids, bases, buffers, chaotropic reagents, surfactants, detergents, sugars, sugar alcohols or any combination thereof.

10. The single reactor according to claim 1, wherein the reactor is a form of column, membrane, eppendorf tube, pipette tip, multi-well plate, magnetic particle or combination thereof.

11. The single reactor according to claim 1, wherein the supporting material is selected from the group consisting of polystyrene, polystyrene/divinylbenzene, silica, controlled porosity glass, dextrans, agarose, acrylates, metals, metal oxides, magnetic support materials, nitrocellulose or combination thereof.

12. The single reactor according to claim 1, wherein a plurality of affinity selectors, enzymes of interest, or combination thereof is used.

13. The single reactor according to claim 11, wherein the supporting material is in a form of particle, monolithic, membrane, planar, microfluidic channel or magnetic support materials.

14. The single reactor according to claim 1, wherein the affinity selected enzyme of interest is treated by reductive alkylation either before or after digestion.

15. The single reactor according to claim 1, wherein said single reactor is operated under dynamic or static heating/shaking conditions.

16. The single reactor according to claim 8, wherein said heat is at a temperature of about 70° C. to produce said activated enzyme.

17. The single reactor according to claim 1, wherein the enzyme of interest is activated by heat to produce an activated enzyme.

18. The single reactor according to claim 17, wherein the activated enzyme is capable of performing enzymatic digestion without pretreatment.

* * * * *

SEQUENCE LISTING

```
<160> NUMBER OF SEQ ID NOS: 2

<210> SEQ ID NO 1
<211> LENGTH: 17
<212> TYPE: PRT
<213> ORGANISM: human

<400> SEQUENCE: 1

Thr Thr Pro Pro Val Leu Asp Ser Asp Gly Ser Phe Phe Leu Tyr Ser
1               5                   10                  15

Lys

<210> SEQ ID NO 2
<211> LENGTH: 16
<212> TYPE: PRT
<213> ORGANISM: human

<400> SEQUENCE: 2

Val Val Ser Val Leu Thr Val Leu His Gln Asp Trp Leu Asn Gly Lys
1               5                   10                  15
```